United States Patent
Chang et al.

(10) Patent No.: US 8,791,557 B2
(45) Date of Patent: Jul. 29, 2014

(54) MICROELECTROMECHANICAL DEVICE WITH INTEGRATED PACKAGE

(71) Applicant: Taiwan Semiconductor Manufacturing Company, Ltd., Hsin-Chu (TW)

(72) Inventors: Allen Timothy Chang, Hsin-Chu (TW); Yi-Shao Liu, Zhubei (TW); Ching-Ray Chen, Taipei (TW); Chun-Ren Cheng, Hsin-Chu (TW)

(73) Assignee: Taiwan Semiconductor Manufacturing Company, Ltd., Hsin-Chu (TW)

( * ) Notice: Subject to any disclaimer, the term of this patent is extended or adjusted under 35 U.S.C. 154(b) by 0 days.

(21) Appl. No.: 13/652,999

(22) Filed: Oct. 16, 2012

(65) Prior Publication Data
US 2013/0293878 A1   Nov. 7, 2013

Related U.S. Application Data

(60) Provisional application No. 61/641,657, filed on May 2, 2012.

(51) Int. Cl.
*H01L 23/02* (2006.01)

(52) U.S. Cl.
USPC ............... 257/678; 257/431; 438/49; 438/57; 438/106

(58) Field of Classification Search
None
See application file for complete search history.

(56) References Cited

U.S. PATENT DOCUMENTS

| | | | |
|---|---|---|---|
| 5,798,557 A * | 8/1998 | Salatino et al. | 257/416 |
| 6,764,875 B2 * | 7/2004 | Shook | 438/106 |
| 6,939,784 B2 * | 9/2005 | Chen et al. | 438/456 |
| 6,953,993 B2 * | 10/2005 | Yamaguchi | 257/704 |
| 6,981,806 B2 * | 1/2006 | Benzoni et al. | 385/94 |
| 2002/0179986 A1 * | 12/2002 | Orcutt et al. | 257/417 |
| 2004/0077117 A1 * | 4/2004 | Ding et al. | 438/51 |
| 2006/0001123 A1 * | 1/2006 | Heck et al. | 257/528 |
| 2007/0181979 A1 * | 8/2007 | Beer et al. | 257/619 |
| 2007/0196239 A1 * | 8/2007 | Vink et al. | 422/82.05 |
| 2007/0235501 A1 * | 10/2007 | Heck | 228/101 |
| 2011/0101533 A1 * | 5/2011 | Yoon et al. | 257/768 |
| 2011/0223279 A1 * | 9/2011 | Kim et al. | 425/385 |

* cited by examiner

*Primary Examiner* — Andres Munoz
(74) *Attorney, Agent, or Firm* — Haynes and Boone, LLP

(57) ABSTRACT

A BioMEMS microelectromechanical apparatus and for fabricating the same is disclosed. A substrate is provided with at least one signal conduit formed on the substrate. A sacrificial layer of sacrificial material may be deposited on the signal conduit and optionally patterned to remove sacrificial material from outside the packaging covered area. A bonding layer may be deposited on at least a portion of the signal conduit and on the sacrificial layer when included. The bonding layer may be planarized and patterned to form one or more cap bonding pads and define a packaging covered area. A cap may be bonded on the cap bonding pad to define a capped area and so that the signal conduit extends from outside the capped area to inside the capped area. Additionally, a test material such as a fluid may be provided within the capped area.

16 Claims, 6 Drawing Sheets

MICROELECTROMECHANICAL DEVICE WITH INTEGRATED PACKAGE

RELATED APPLICATIONS

This application claims priority to U.S. Provisional Application No. 61/641,657, filed on May 2, 2012, entitled which is herein incorporated by reference.

BACKGROUND

BioMEMS devices are microelectromechanical systems which have a sensing element for biological applications, and often have an optical or electrical signal conduit that connects between a packaged fluidic device and the outside environment. A cap enclosing the packaged fluidic device from the outside environment is frequently used, with the cap bonded directly over the optical signal conduits as they run to fluidic material retained by the cap. Traditionally, adhesive bonding with polydimethylsiloxane ("PDMS") or anodic bonding might be used to bond the cap over the signal conduit, but this requires the conduit introduce a minimal topography change (for example, <1000 angstroms in the case of anodic bonding). Use of PDMS as the bonding agent, bonding directly on the conduit, has been commonly used, as the index of refraction is similar to $SiO_2$ and therefore does not interfere with optical signal conduit operation. Generally, this BioMEMS system using PDMS is easy to prototype and does not require a cleanroom environment. However, in some cases PDMS introduces conduit topography contribution limitations that generally require the signal conduit to be less than 200 nanometers high because the PDMS cannot securely bond over a greater topography variation. Additionally, PDMS absorbs molecules such as fluorophores in capped areas critical for signal generation, and, in certain situations, may be too porous, allowing water to evaporate thought the seal.

Additionally, anodic bonding, or bonding directly on the conduit via an electrostatic field, requires high voltage, particularly for a conduit thicker than a few hundred angstroms, typically requiring around 800V-1000V to achieve a proper bond. The high energy associated with such anodic bonding can change the physical properties of the optical or electrical conduit, making it less efficient or otherwise unsuitable. Additionally, anodic bonding suffers from conduit topography contribution limitation (<100 nm) as well, and sometimes requires a temperature up to about 400 to 500 degrees Celsius, which may make it incompatible for BioMEMS device fabrication on a CMOS wafer.

Other methods used in the adhesive bonding technique of a fluidic device include using glue or epoxy to bond a polycarbonate cap directly on to the conduit. However, these materials used in such a technique may interfere with the function of the signal conduit.

BRIEF DESCRIPTION OF THE DRAWINGS

For a more complete understanding of the present embodiments, and the advantages thereof, reference is now made to the following descriptions taken in conjunction with the accompanying drawings, in which.

DETAILED DESCRIPTION OF ILLUSTRATIVE EMBODIMENTS

The making and using of the present embodiments are discussed in detail below. It should be appreciated, however, that the present disclosure provides many applicable inventive concepts that can be embodied in a wide variety of specific contexts. The specific embodiments discussed are merely illustrative of specific ways to make and use the disclosed subject matter, and do not limit the scope of the different embodiments. Embodiments will be described with respect to a specific context, namely a system and method for creating a BioMEMS device structure.

Disclosed herein is a method for creating, and a device for use in, BioMEMS packaged applications, and microfluidics in particular. The embodiments disclosed herein avoid signal conduit interference or damage and overcome the topography imposed by the signal conduit. The signal conduit allows control or sensing between inside and outside the package or capped area. Drawings illustrating the presented principles are described herein, but are not meant to be limiting, and are not drawn to scale.

Figure 1:
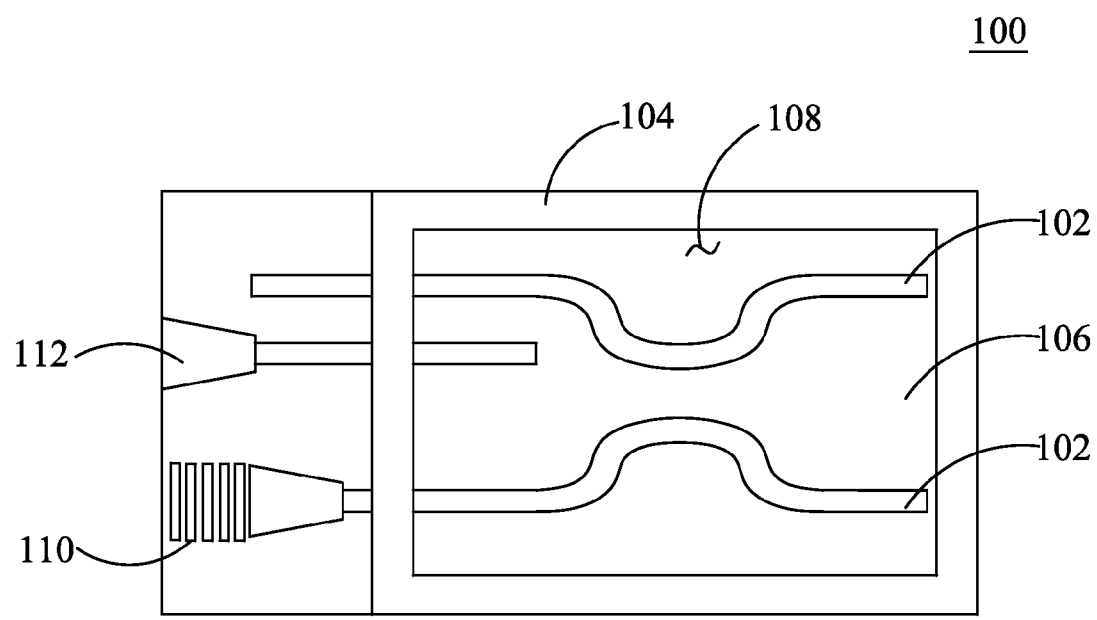
FIG. 1 is a top view diagram illustrating application of a cap over signal conduits.

FIG. 1 is a top view diagram illustrating an application of a cap over optical conduits according to the present disclosure, resulting in a BioMEMS device structure 100. A substrate 106 may have one or more signal conduits or waveguides 102, that may optionally be optical or electrical, disposed thereon, with input structures configured to couple an input source to the signal conduit. The input structure may be a coupling structure, such as, but not limited to, a grating coupler 110 or cable bonding structure 112 acting as an interface between a light source and optical signal conduits 102. Alternatively, the signal conduits 102 may conduct an electrical signal to send electrical signals or power into the capped area 108 or collect signals from inside the capped area 108, and the input structure may be configured to mount an electrical connection such as a wire or interconnect. For example, the signal conduits 102 may interact with material inside the capped area 108. In some embodiments, the signal conduits 102 may measure impedance by applying AC voltage and measuring current through material in the capped area 108.

Cap walls 104 may be disposed over the signal conduits 102 to define and contain an enclosed, capped area 108. The capped area 108 may be configured to enclose a volume and retain a controlled environment in contact with the signal conduit 102. For example, the capped area 108 may be a fluid reservoir, or may contain gaseous environment, or any combination of materials. In one useful embodiment, the capped area 108 may be at least partially filled with a fluid, and the fluid may have a material for testing. Skilled artisans will recognize that while the principles presented herein are described in part as referring to light and the transmission of the same, that any frequency of electromagnetic radiation may be advantageously used in the described embodiments. Thus, infrared and ultraviolet radiation, radio transmissions, x-rays, gamma rays, and any other radiation may be substituted for visible light.

Figure 2A:
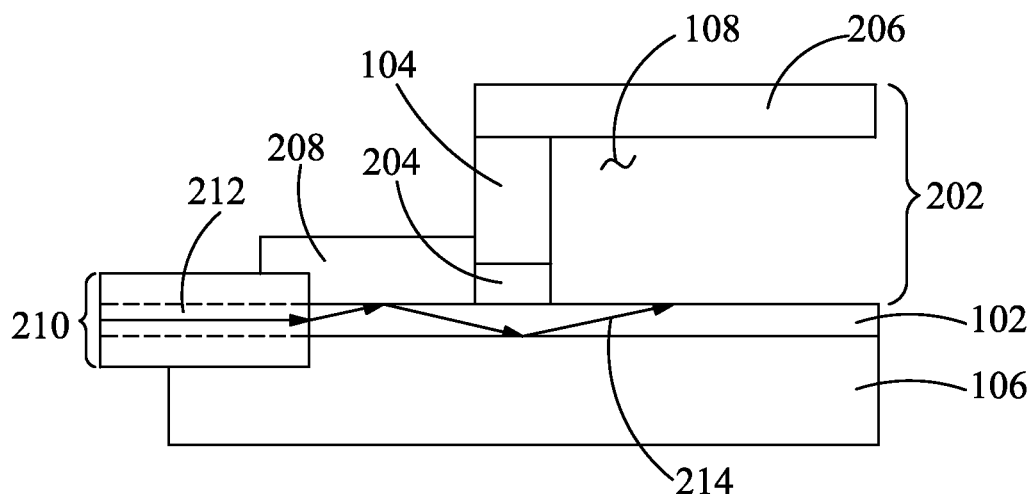
FIGS. 2A and 2B are side view diagrams illustrating optical conduits and optical inputs disposed under a cap and within a capped area.

FIG. 2A is a side view diagram illustrating an embodiment of a portion 200 of a BioMEMS device structure where a signal conduit 102 is disposed under a cap 202 and within a capped area 108. The signal conduit has an optical cable 210 input outside the capped area 108. A cap 202 with cap walls 104 and cap top 206 may be disposed over a cap bonding pad 204 to define the capped area 108. Thus, the cap 202 may keep the test material separate from an outside environment and prevent contamination.

The signal conduit 102 may be formed on the substrate 106 and under the cap 202, with the cap bonding pad 204 separating the cap 202 from the signal conduit 102. An optical cable 210 may be attached to the substrate 106 so that an optical core 212 of the optical cable 210 provides an optical path for incoming light 214 to the signal conduit 102. The optical cable 210 may be attached and held in place by an adhesive 208 such as PDMS, by an adhesive fastening system, via anodic bonding, via fusion bonding, or by another bonding or attachment system.

Additionally, the cap 202 defining the capped area 108 may have one or more openings for introducing test material. Thus, a BioMEMS test device may be produced without any particular environment inside the capped area 108, and then a sample may be captured in the capped area 108 at a later point.

Figure 2B:
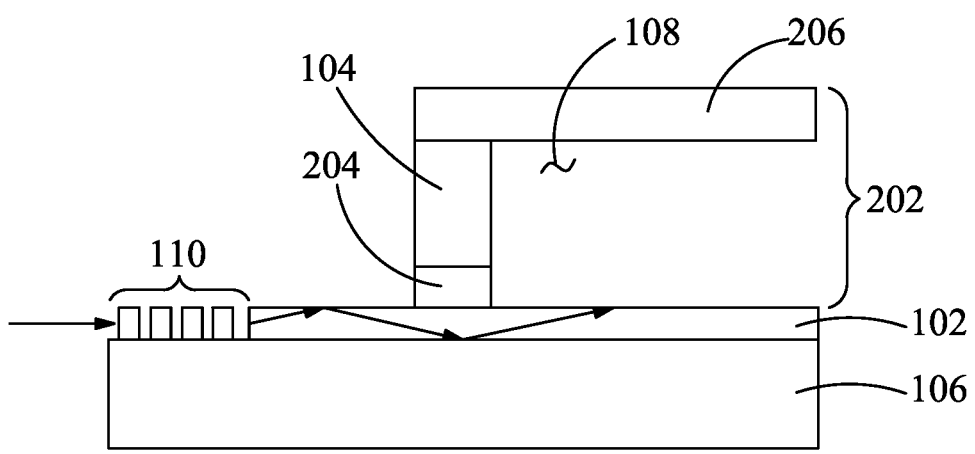

FIG. 2B is a side view diagram illustrating an alternative embodiment of a portion 220 of a BioMEMS device structure where an optical conduit 102 is disposed under a cap 202 and within a capped area 108. The conduit has a grating coupler 110 outside the capped area 108. In such an embodiment, a laser or other light source may be provided remotely, and may be directed into the grating coupler 110 wherein it is transmitted into the optical conduit 102.

Figure 3A:
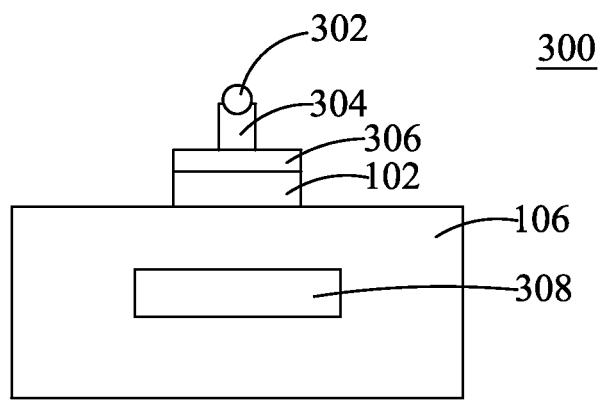
FIGS. 3A-3B are cross-sectional diagrams illustrating use of embodiments of fluidic devices.
Figure 3B:
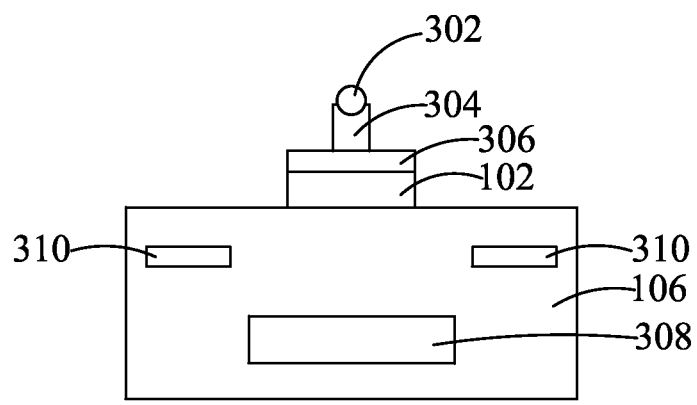

FIG. 3A is a cross-sectional diagram illustrating operation of the sensing portion 300 of an embodiment of a BioMEMS device structure. A photodetector 308 or other photosensitive device, such as, but not limited to, a photodiode, active pixel sensor, phototransistor, photoresistor, charge coupled device, or the like, may be disposed in the substrate 106. Alternatively, an electrical or chemical sensor may be disposed in or on the substrate and may be configured to detect a property or reaction by the target molecule 302 when interacting with the signal conduit 102. The optical conduit 102 may also be advantageously disposed on the surface of the substrate 106, and may have a surface chemistry layer 306 and a receptor 304 configured to interact with a particular or predetermined type of target molecule 302. A surface chemistry layer 306 may optionally be disposed on the signal conduit 102 or at any other advantageous location in the capped area 108, and may be configured to attract or interact with the target molecule 302. Alternatively, the surface chemistry 306 may be a filter and may be specifically tuned to filter light fluorescing from the target molecule 302. A receptor 304 may advantageously be a molecule, protein, antibody, enzyme, polymerase, bacteria, cells, or the like. A target molecule 302 may, for example, be an analyte with a fluorescent dye, or alternatively, may be a fluorescent protein, fluorescently tagged antibody, fluorescently tagged DNA, or the like. A light transmission such as an evanescent wave from the signal conduit 102 excites a fluorescent dye, tag, or protein in the target molecule 302 and the fluorescent response from the target molecule 302 is detected by the photodetector 308. As shown in FIG. 3B, one or more electrodes 310 may be disposed at the substrate 106. For example, the electrode 310 may be, but is not limited to being, disposed on the surface of the substrate 106, or contained within the substrate 106.

The electrodes 310 may be configured to interact with the target molecule 302, by, for example, controlling, or taking data readings from the target molecule 302. In one embodiment, the electrodes 310 may resistively heat a fluid or environment contained in the capped area 108. In an alternative embodiment, the electrodes 310 may have an AC voltage applied to help guide the analyte or target molecule 302 to the signal conduit 102 or receptor 304 by dielectrophoresis. In another embodiment, the electrodes 310 may be configured to read electrical characteristics of target molecule 302 or material in the capped area 108. For example, the electrodes 310 may apply an AC voltage to the capped area 108, and read an impedance or current from the capped area 108.

Figure 4A:
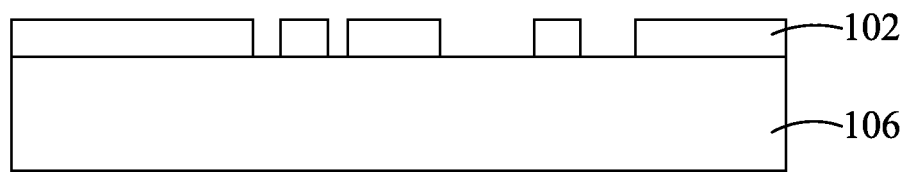
FIGS. 4A-4F and 5A-5B are diagrams illustrating embodiments of a method for creating a BioMEMS device structure.

FIGS. 4A-4F and 5A-5B are cross sectional views of a BioMEMS device structure 400 at various stages of manufacture according to one or more embodiments. Initially, FIG. 4A illustrates a BioMEMS device structure 400 in an early stage of manufacture. A signal conduit 102 may be disposed on a substrate 106, with the substrate 106 being a material such as, but not limited to, glass, silicon (Si), gallium arsenide (GaAs), fiberglass, metal, or the like. Additionally, the substrate 106 may optionally contain circuitry such as CMOS devices; interconnect lines, sensors, electrodes, photodetectors, doped regions, or the like. In one embodiment, the signal conduit 102 may be patterned to disperse light, or to provide separate conduit sections. An optical signal conduit 102 may, for example, be a high-k material such as silicon nitride ($Si_3N_4$), silicon oxynitride (SiON), hafnium dioxide ($HfO_2$), tantalum pentoxide ($Ta_2O_5$), or the like. Alternatively, an electrical signal conduit 102 may, for example, be a metal or other conductive material, such as gold (Au), aluminum (Al), copper (Cu), titanium nitride (TiN), alloys of the same, or the like. A typical signal conduit 102 thickness may be between about 500 angstroms and about 6000 angstroms. In one embodiment of the presented principles, dry etching technique may be employed to pattern the optical signal conduit 102, and may provide better optical conduit critical dimension control than wet etching. Additionally, some embodiments may have an optical signal conduit 102 with a smooth outer surface, resulting in more efficient transmission of an optical signal.

Figure 4B:
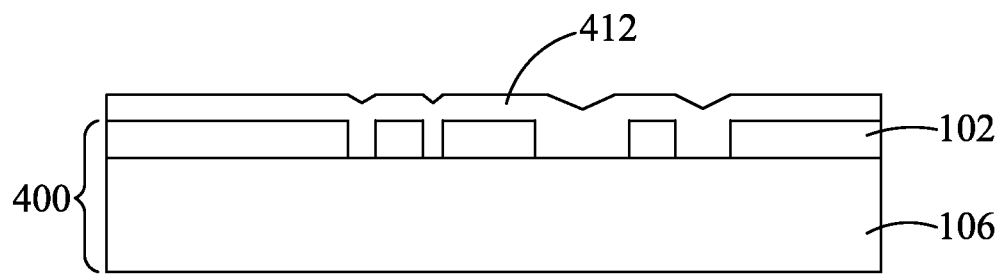

FIG. 4B illustrates a cross-sectional view of a BioMEMS device structure 400 after forming a sacrificial layer 412. In one embodiment, a sacrificial layer 412 may be a hard, or non-polymer, material such as germanium (Ge), silicon (Si), titanium tungsten alloy (TiW), aluminum (Al), or the like, and may advantageously be deposited over the substrate 106 and signal conduit 102 by plasma vapor deposition, chemical vapor deposition, physical vapor deposition, or the like. In one embodiment, the sacrificial layer 412 may have a thickness between about 2000 angstroms and about 6000 angstroms.

Figure 4C:
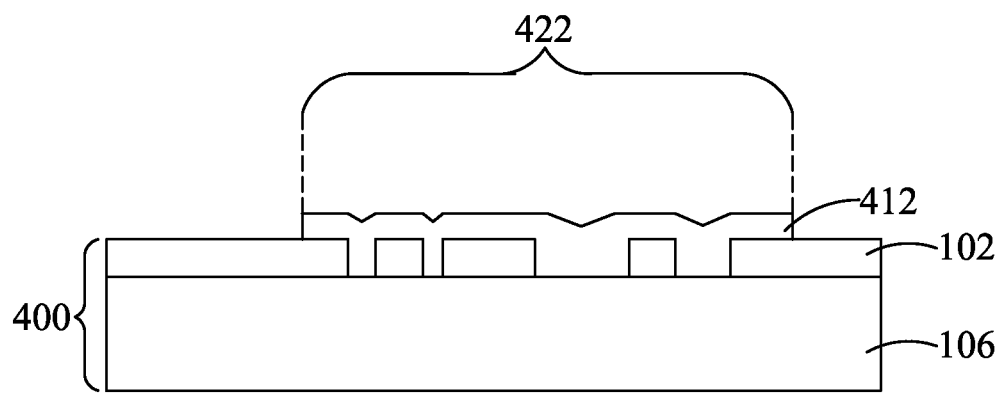

FIG. 4C illustrates a cross-sectional view of a BioMEMS device structure 400 after patterning the sacrificial layer 412. The sacrificial layer 412 may be patterned or removed from regions outside of the future packaging covered area 422 via lithography, or any other suitable process, leaving sacrificial layer 412 material only in the packaging covered area 422. Removal of the sacrificial layer 412 may be accomplished by an etchant appropriate for the particular sacrificial layer 412 material, including, but not limited to, hydrogen peroxide ($H_2O_2$), phosphoric acid ($H_3PO_4$), potassium hydroxide (KOH), tetramethylammonium hydroxide (TMAH), ethylenediamine pyrocatechol (EDP), xenon diflouride ($XeF_2$), and the like.

Figure 4D:
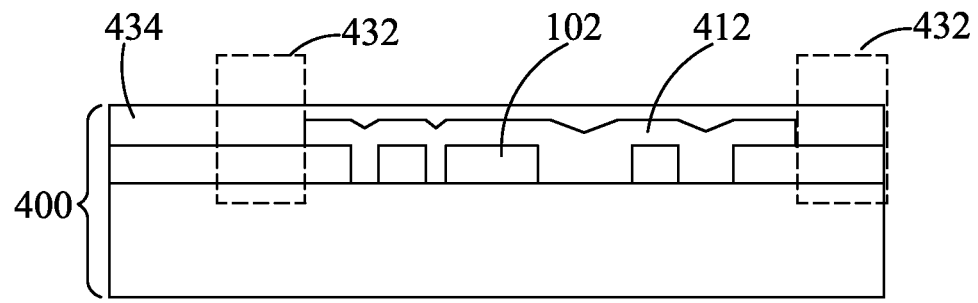

FIG. 4D illustrates a cross sectional view of a BioMEMS device structure 400 after forming a bonding layer. A bonding layer 434 may be deposited over the patterned sacrificial layer 412 and signal conduit 102. In one embodiment, the bonding layer 434 may be applied so that it lies in the bonding area 432 to cover the signal conduit 102 and provide a pad for bonding a cap wall 104 over the signal conduit 102. The bonding layer 434 may be, in some embodiments, an oxide such as silicon dioxide or the like, and may be deposited via, for example, a chemical vapor deposition process, a plasma enhanced deposition process, or any other suitable process. Alternatively, the bonding layer 434 may be a nitride, a metal layer, a polysilicon layer, or the like, and the bonding layer material may be selected depending on the signal conduit 102 properties.

The sacrificial layer 412 may shield the signal conduits 102 from an overlying bonding layer 434, in the region where the bonding layer 434 will later be removed.

In one embodiment of the present principles, it may be advantageous to have a hard sacrificial layer 412 instead of a sacrificial photoresist (PR) under the bonding layer 434 because polymer residues could interfere with the surface chemistry 306 of the BioMEMS device sensing structure. Additionally, the planarization of bonding layer 434 that would be deposited on a sacrificial photoresist layer may be problematic because the oxide is on a soft material: the stress and pressure from planarization may cause a polymer-type photoresist to deform and the bonding layer to fail during the planarization. However, a biocompatible photoresist may be used, and the chemistry of such a biocompatible photoresist may be determined by the test material intended for the capped area 108. In such an instance, a biocompatible photoresist chemistry will preferably be selected to not interfere with the testing procedure and chemistry of any target molecule 302.

The bonding layer 434 may be deposited at a thickness over the substrate 106 surface between about 4 micrometers (40,000 angstroms) and 0.5 micrometers (5,000 angstroms) and may be subsequently planarized, using for example, a chemical mechanical polish, down to a thickness between about 2 micrometers (20,000 angstroms) and about 0.4 micrometers (4,000 angstroms). The bonding layer 434 may provide a planarized surface capable of accepting a range of bonding technologies while permitting an signal conduit 102 thickness up to about 600 nanometers (6,000 angstroms). Thus, one useful embodiment may be where the signal conduit is between about 200 nanometers (2,000 angstroms) and about 600 nanometers (6,000 angstroms) thick, and the bonding layer covers the signal conduit 102 while having a planarized bonding surface.

Figure 4E:
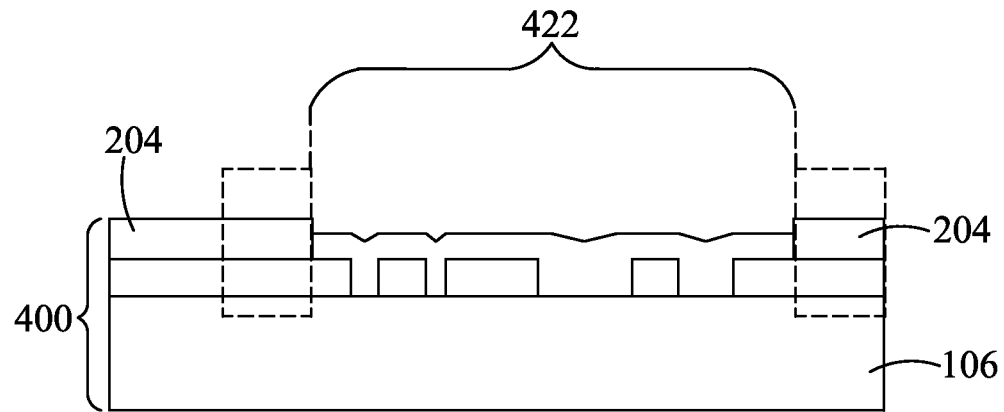

FIG. 4E illustrates a cross sectional view of BioMEMS device structure 400 after patterning the bonding layer 434. The bonding layer 434 may be patterned or formed into cap bonding pads 204 by etching to remove the bonding layer 434 material in order to define or form a packaging covered area 422, with bonding layer 434 material remaining in the bonding areas 432 as a target for bonding cap walls 104. In one particularly useful embodiment, the bonding layer 434 may be etched using a dry etch technique, such as plasma etching or ionic sputtering. Alternatively, and depending on the bonding layer 434 material, a wet etch, or any other type of etching, may be advantageously employed to pattern the bonding layer 434. In one embodiment, the bonding layer 434 may be planarized prior to patterning, which may avoid damage or contamination of portions of the substrate or signal conduit that may be unintentionally exposed from topography-induced insufficient mask or photoresist coverage during patterning. Additionally, planarizing the bonding layer 434 prior to patterning reduces or prevents damage or destruction by planarization of regions whose bonding layer has been patterned away.

Figure 4F:
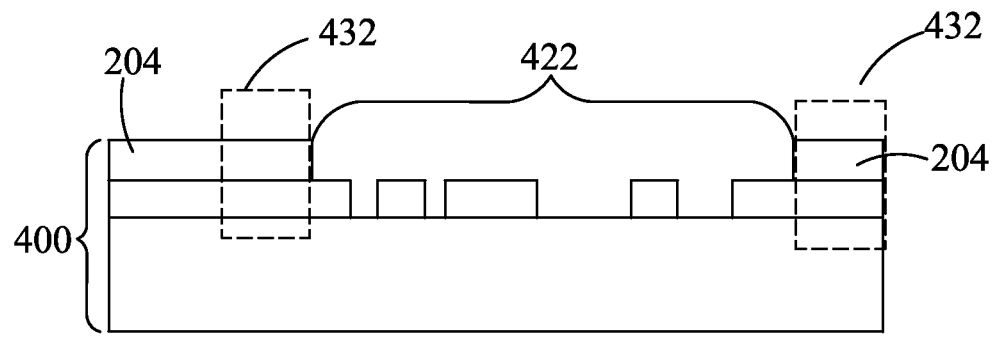

FIG. 4F illustrates a cross-sectional view of a BioMEMS device structure 400 after the sacrificial layer 412 is removed, exposing the signal conduit 102. Removal of the sacrificial layer 412 may be performed by, for example, a wet or vapor etch in a similar manner as described above for the sacrificial layer 412 patterning. Thus, the signal conduit 102 is exposed in the packaging covered area 422.

Figure 5A:
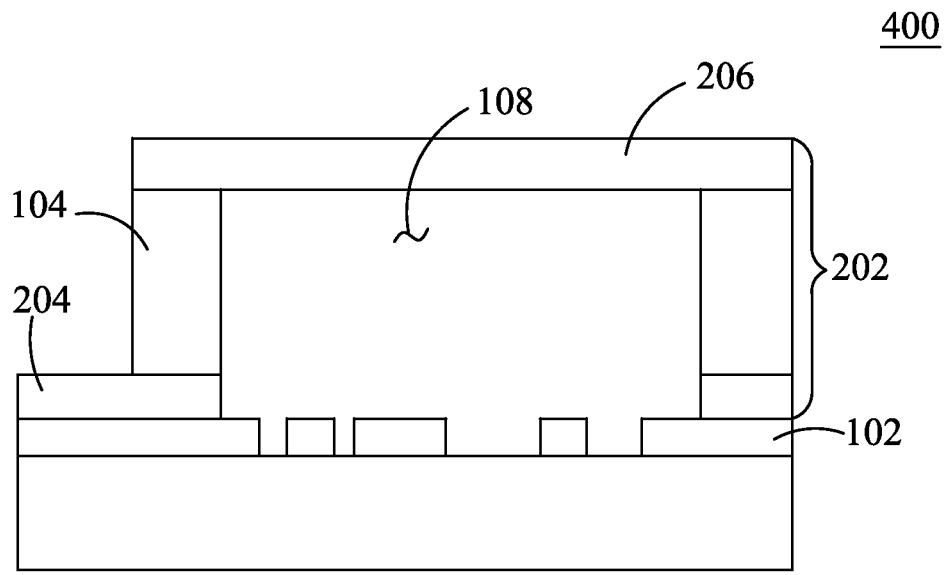
Figure 5B:
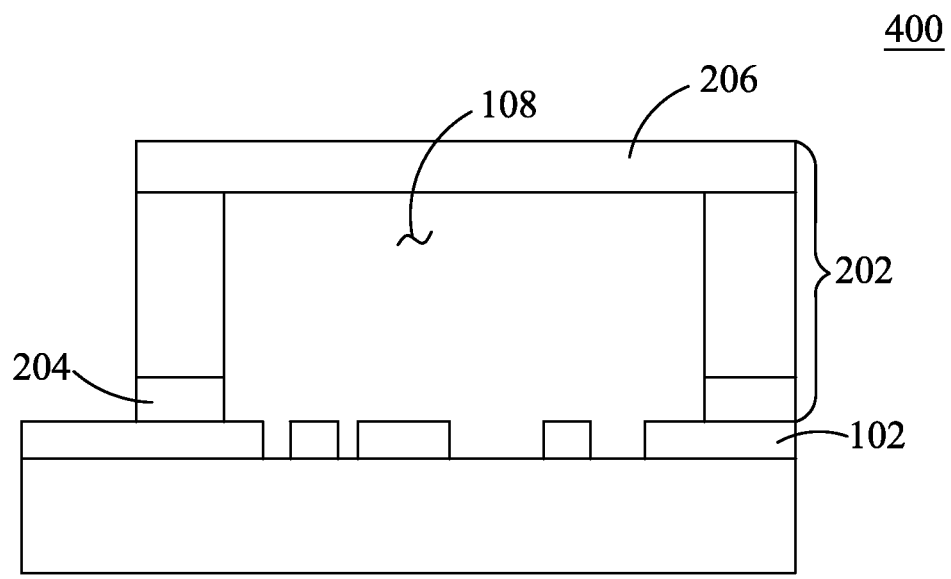

FIGS. 5A and 5B illustrate a BioMEMS device structure 400 with a cap 206 bonded according to one or more embodiments of the disclosure. FIG. 5A illustrates an embodiment of a BioMEMS device structure 400 with cap bond pads 204 disposed under the cap wall 104 and covering the signal conduit 102 outside of the capped area 108. FIG. 5B illustrates an embodiment of a BioMEMS device structure 400 with cap bond pads 204 disposed in the area under the cap wall 104 but exposing the exterior portions of the signal conduit 102. The cap bond pad 204 and sacrificial material 412 remaining outside the capped area may be removed to expose the exterior portion of the signal conduit 102 during the steps illustrated in FIGS. 4B through 4F. Alternatively, the exterior portion of the signal conduit 102 may be exposed in a separate step, for example, after the cap 202 is applied to the cap bond pads 204.

The cap wall 104 may be bonded to the cap bonding pads 204 using an adhesive such as an epoxy, via fusion bonding, or any other suitable technique. In one useful embodiment, for example, fusion bonding with low temperature (<300 C) anneal may be suitable where the cap bonding pad 204 material is an oxide. The cap top 206 may be bonded to the cap wall 104 to form the cap 202 and define the capped area 108. The capped area 108 may be provided with a gaseous environment or fluidic material prior to bonding the cap top 206, or via a sealable opening after the cap top 206 is bonded. The cap 202 will preferably be configured to remain water- or liquid-tight in an embodiment where the capped area maintains a fluidic material. Likewise where the capped area 108 maintains a gaseous material, the cap 202, including the cap's structures and bonded seams will be gas-impermeable.

Separation of the bonding material and cap walls 104 from the signal conduit 102 by the cap bonding pads 204 permits a planar bonding surface, since the bonding layer 434 and cap bonding pads 204 are laid over the signal conduit 102 and substrate 106 and then planarized. As the bonding pad 204 is planarized, the cap bonding pad 204 may be used to compensate for irregularities that may exist on the surface of the signal conduit 102 as well as on the substrate 106. Skilled artisans will recognize that in order to maintain a suitable planar surface, the cap bonding pads 204 will be at least as thick as the signal conduit 102 is high so that the cap bonding pads 204 lie on top of the signal conduit 102. In particularly useful embodiments, the signal conduit 102 will be less than about 600 nanometers, with the planarized cap bonding pads 204 being thicker than the signal conduit 102.

Thus, in order to form a BioMEMS microelectromechanical apparatus a practitioner may provide a substrate and deposit at least one signal conduit disposed on the substrate. A sacrificial layer 412 may be deposited on the signal conduit and optionally patterned to remove sacrificial layer 412 material from outside the packaging covered area 422. A bonding layer 434 may be deposited on at least a portion of the signal conduit and on the sacrificial layer 412 when included. The bonding layer 434 may be planarized and patterned to form one or more cap bonding pads 204 and define a packaging covered area 422. A cap 202 may be bonded on the cap bonding pad 204 to define a capped area 108, and so that the signal conduit extends from outside the capped area 108 to inside the capped area 108. Additionally, a test material such as a fluid may be provided within the capped area 108.

In useful embodiments, and in particular embodiments having an optical signal conduit 102, using a bonding technique other than PDMS adhesive avoids fluorophore absorption and porosity issues that affect signal detectability in a bio-optical fluidic system. Additionally, when epoxy is applied directly to an optical signal conduit 102 as a bonding material, the epoxy's index of refraction may interfere with optical signal conduit 102. Use of an oxide as the bonding layer 434 and subsequent cap bonding pads 204 may be advantageous on an optical signal conduit as oxide usually has lower index of refraction than the signal conduit, and thus, the oxide does not interfere with the signal conduit's 102 propagation of optical signals, avoiding the problems associated with epoxy as a bonding material.

Although the present embodiments and their advantages have been described in detail, it should be understood that various changes, substitutions, and alterations can be made herein without departing from the spirit and scope of the disclosure as defined by the appended claims. For example, many of the features and functions discussed above can be implemented on various substrates and as packaging for a variety of enclosed systems, particularly those having surface mounted optical signal conduits. As another example, it will be readily understood by those skilled in the art that the topography of conduits, number of conduits, purpose of conduits, and conduit material may be varied while remaining within the scope of the present disclosure.

Moreover, the scope of the present application is not intended to be limited to the particular embodiments of the process, machine, manufacture, composition of matter, means, methods, and steps described in the specification. As one of ordinary skill in the art will readily appreciate from the disclosure, processes, machines, manufacture, compositions of matter, means, methods, or steps, presently existing or later to be developed, that perform substantially the same function or achieve substantially the same result as the corresponding embodiments described herein may be utilized according to the present disclosure. Accordingly, the appended claims are intended to include within their scope such processes, machines, manufacture, compositions of matter, means, methods, or steps.

What is claimed is:

1. A microelectromechanical device, comprising:
at least one optical signal conduit disposed on a substrate;
at least one cap bonding pad disposed on the substrate and over a portion of the at least one optical signal conduit, the at least one cap bonding pad being formed of a polymer free material, the at least one cap bonding pad including a planarized top surface, the at least one cap bonding pad partially defining a cavity; and
a cap bonded to the at least one cap bonding pad, and covering the cavity thereby forming a capped area having a controlled environment; and
an adhesive disposed on a sidewall of the at least one cap bonding pad and on a sidewall of the cap,
wherein the at least one optical signal conduit extends from outside the capped area to inside the controlled environment of the capped area.

2. The device of claim 1, further comprising a receptor disposed within the capped area operable to interact with a predetermined type of target molecule.

3. The device of claim 1, further comprising a photodetector disposed at the substrate, wherein the at least one optical signal conduit is operable to transmit light to a target molecule and wherein the photodetector is operable to detect a response from the target molecule.

4. The device of claim 1, wherein the at least one cap bonding pad is an oxide having an index of refraction lower than the index of refraction of the at least one optical signal conduit.

5. The device of claim 1, wherein the capped area is at least partially filled with a fluid test material.

6. The device of claim 1, wherein the at least one cap bonding pad is thicker than the at least one optical signal conduit.

7. The device of claim 1, wherein the cap is bonded to the planarized top surface of the at least one cap bonding pad by fusion bonding.

8. A microelectromechanical device, comprising:
an optical signal conduit disposed on a substrate;
a pad disposed over the substrate and over a portion of the optical signal conduit, the pad being formed of a polymer free material;
an input structure coupled to the optical signal conduit;
a cap disposed over the pad and over the optical signal conduit inside a controlled environment of a capped area; and
an adhesive disposed on the input structure, on a sidewall of the pad, and on a sidewall of the cap.

9. The device of claim 8, further comprising a surface chemistry layer disposed within the capped area operable to interact with a target molecule.

10. The device of claim 9, further comprising a receptor disposed within the capped area operable to interact with the target molecule, wherein the target molecule is a predetermined type of target molecule.

11. The device of claim 9, further comprising one or more electrodes disposed at the substrate operable to interact with the target molecule.

12. The device of claim 8, wherein the pad is thicker than the optical signal conduit.

13. The device of claim 8, wherein the cap is bonded to the pad by fusion bonding.

14. A microelectromechanical device, comprising:
an optical signal conduit disposed on a substrate;
a bonding pad structure disposed over the substrate and over a top surface of the optical signal conduit, wherein the bonding pad structure is formed of a polymer free material, wherein the bonding pad structure extends through a closed path and partially bounds a cavity;
a cap including a top structure and a wall structure, wherein the wall structure is bonded to the bonding pad structure and extends through the closed path and partially bounds the cavity, and wherein the top structure is disposed over the wall structure and covers the cavity thereby defining a controlled environment; and
an adhesive disposed on a sidewall of the bonding pad structure and on a sidewall of the wall structure.

15. The device of claim 14, wherein the optical signal conduit extends from outside the controlled environment to inside the controlled environment, and
wherein the top structure is disposed over the optical signal conduit inside the controlled environment.

16. The device of claim 14, wherein the bonding pad structure is thicker than the optical signal conduit.

* * * * *